United States Patent
Fordham (10) Patent No.: US 10,209,324 B2
(45) Date of Patent: Feb. 19, 2019

(54) SAMPLE HOLDER FOR USE IN NMR (71) Applicant: SCHLUMBERGER TECHNOLOGY CORPORATION, Sugar Land, TX (US)

(72) Inventor: Edmund J. Fordham, Cambridge (GB)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 1500 days.

(21) Appl. No.: 13/920,897

(22) Filed: Jun. 18, 2013

(65) Prior Publication Data
US 2013/0335081 A1 Dec. 19, 2013

(30) Foreign Application Priority Data

Jun. 19, 2012 (GB) .................................. 1210808.0

(51) Int. Cl.
*G01R 33/30* (2006.01)
*G01N 24/08* (2006.01)

(52) U.S. Cl.
CPC ......... *G01R 33/305* (2013.01); *G01N 24/081* (2013.01)

(58) Field of Classification Search
USPC .................. 324/300–322; 600/407–435; 382/128–132
See application file for complete search history.

(56) References Cited

U.S. PATENT DOCUMENTS

| 6,229,308 B1 | 5/2001 | Freedman |
| 6,507,191 B1 * | 1/2003 | Eguchi ................. G01R 33/305 324/305 |
| 7,352,179 B2 | 4/2008 | Chen et al. |

(Continued)

FOREIGN PATENT DOCUMENTS

| CA | 2631089 | 1/2012 |
| GB | 2489005 | 9/2012 |

OTHER PUBLICATIONS

GB Patent Office Examination Report for corresponding GB Application Serial No. 1210808.0, dated Sep. 15, 2016, 4 pages.
(Continued)

*Primary Examiner* — Melissa Koval
*Assistant Examiner* — Tiffany Fetzner (57) ABSTRACT

A pressurizable holder for a sample to be examined by NMR, comprises a pressure retaining nonmagnetic tube surrounding a radio-frequency coil which in turn surrounds a space for the sample. The pressure retaining tube is formed of (i) nonmetallic electrically insulating material such as a ceramic or (ii) nonmetallic electrically insulating matrix material reinforced with electrically insulating filaments such as glass fiber, or (iii) non-metallic electrically insulating matrix material reinforced with electrically conductive filaments configured so that conductivity is anisotropic. There is good coil filling factor without constraint on wall thickness of the pressure retaining tube. Avoidance of isotropically conductive material inhibits eddy currents when an NMR spectrometer's magnetic field gradient coils are switched on and off. The tube resists hoop stress from internal pressure. Longitudinal stress is resisted by structure connecting end pieces at the ends of the pressure retaining tube.

15 Claims, 5 Drawing Sheets

(56) References Cited

U.S. PATENT DOCUMENTS

| | | | |
|---|---|---|---|
| 8,123,888 B2* | 2/2012 | Hammami | B29C 53/8016 156/169 |
| 2004/0254419 A1* | 12/2004 | Wang | A61K 45/06 600/8 |
| 2005/0025797 A1* | 2/2005 | Wang | A61L 31/16 424/422 |
| 2005/0079132 A1* | 4/2005 | Wang | A61L 31/082 424/1.11 |
| 2005/0107870 A1* | 5/2005 | Wang | A61L 31/10 623/1.44 |
| 2007/0010702 A1* | 1/2007 | Wang | A61F 2/82 600/8 |
| 2007/0038076 A1 | 2/2007 | Osada et al. | |
| 2009/0128144 A1* | 5/2009 | Freedman | G01N 24/081 324/303 |
| 2009/0200013 A1 | 8/2009 | Craster et al. | |
| 2009/0236091 A1* | 9/2009 | Hammami | B29C 53/8016 166/242.1 |
| 2011/0050223 A1 | 3/2011 | Balcom et al. | |
| 2012/0092008 A1 | 4/2012 | Krioutchkov et al. | |
| 2013/0335081 A1* | 12/2013 | Fordham | G01R 33/305 324/309 |
| 2014/0091800 A1* | 4/2014 | Fordham | G01R 33/305 324/321 |

OTHER PUBLICATIONS

Search Report of British Application No. 1210808.0 dated Sep. 17, 2012: pp. 1-2.

Search Report of British Application No. 1210808.0 dated Jan. 28, 2013: pp. 1-2.

"2010 Model Elevated Temperature Triaxial core Flow Cell System," ErgoTech Ltd., 2010: p. 1.

Fordham et al., "Imaging Multiexponential Relaxation in the (y, loge T1) Plane, with Application to Clay Filtration in Rock Cores," Journal of Magnetic Resonance, Seriies A, 1995, vol. 113: pp. 139-150.

Goodyear et al., "Single point measurements of magnetic field gradient waveform," Journal of Magnetic Resonance, 2003, vol. 163: pp. 1-7.

Grammitikos et al. "On the electrical properties of multi scale reinforced composites for damage accumulation monitoring," Composites: Part B, 2012: pp. 1-10.

Green, "Capillary Pressure Curves Determined by Direct Measurement of the Saturation using Magnetic Resonance Imaging," CWLS Magazine InSite, May 2009, vol. 28(1) : pp. 20-25.

Hoult et al., "The Signal-to-Noise Ration of the Nuclear Magnetic Resonance Experiment," Journal of Magnetic Resonance, 1976, vol. 24: pp. 71-85.

J. Cano Barrita et al., "OTC 19234: Capillary Pressure Measurement in Petroleum Reservoir Cores with MRI," Offshore Technology Conference, May 2008: pp. 1-11.

Menana et al., "3-D Eddy Current Computation in Carbon-Fiber Reinforced Composites, IEEE Transactions on Magnetics," Mar. 2009, vol. 45(3): pp. 1008-1011.

Park et al.,"Quantitative evaluation of the electrically conductive internal network in CFRP composites," Proceedings of SPIE, 2002, vol. 4704: pp. 40-50.

Park et al., "Experimental and numerical study of the electrical anisotropy inunidirectional carbon-fiber-reinforced polymer composites," Smart Mater. Struct., Feb. 2007, vol. 16(1): pp. 57-66.

Pratap et al., "Eddy Currents in Anisotropic Composites Applied to Pulsed Machinery," IEEE Transactions on Magnetics, Mar. 1996, vol. 32(2): pp. 437-444.

Schueler et al., "Damage detection in CFRP by electrical conductivity mapping," Composites Science and Technology, 2001, vol. 61: pp. 921-930.

Taipalus et al., "The electrical conductivity of carbon-fibre-reinforced polypropylene/polyaniline complex-blends: experimental characterisation and modelling," Composites Science and Technology, 2001, vol. 61: pp. 801-814.

"Technox Zirconia," Dynamic-Ceramic Ltd., retrieved Jun. 16, 2012: pp. 1-2.

"Technox Zirconia Ceramics," Dynamic-Ceramic Ltd., retrieved Jun. 16, 2012: p. 1.

\* cited by examiner

SAMPLE HOLDER FOR USE IN NMR

CROSS-REFERENCE TO RELATED APPLICATION

This application claims priority to British Application no. 1210808.0 filed Jun. 19, 2012, which is incorporated herein by reference in its entirety.

BACKGROUND

One technology for examining properties of a solid or liquid sample is nuclear magnetic resonance (NMR) also referred to as magnetic resonance imaging (MRI). There are circumstances where a sample is examined under pressure, thus requiring a sample holder which can contain the sample under pressure while it is in the magnetic field of an NMR spectrometer.

A category of samples for which examination under pressure may be required is solid and also liquid samples collected below ground. When drilling through underground rock, it is common practice to drill around a cylinder of rock which is subsequently brought to the surface as a sample, habitually referred to as a rock core. Once brought to the surface, rock cores may be subjected to various measurements and tests. Tests which have been carried out include examination by nuclear magnetic resonance (NMR) also referred to as magnetic resonance imaging (MRI) which entails placing the core within a magnetic field and using one or more radio-frequency coils to apply radio-frequency energy to the core and receive radio-frequency signals from it.

The subterranean rock formations from which such cores are taken are of course at high pressure and it can be desirable to carry out NMR measurements while the sample is under pressure. Liquid samples brought to the surface may also be subjected to NMR measurements whilst still under pressure.

Design of a sample holder which can retain pressure and which can be placed in the magnetic field of an NMR spectrometer needs to address several issues, including mechanical construction for containing pressure, choice of materials to enable the core to be exposed to both magnetic field and radio-frequency, and positioning of the core holder in relation to the functional components (i.e., magnets and coils) of an NMR spectrometer.

A pressurizable core holder which is available from ErgoTech Ltd, Conwy, Wales uses a tube of glass fiber reinforced composite to contain a core under pressure. Compressive force applied to the ends of the tube opposes stress longitudinally relative to the pressurized tube. The radio-frequency coil and the magnets of an NMR spectrometer are positioned outside the tube in spaces between the tube and tie rods connecting the structural parts which apply compressive force to the ends of the tube. In this arrangement, where the magnets fit between the tube and the tie rods, the tie rods are spaced apart in the direction of the magnetic field and the spacing between them has to be greater than the distance between the magnets.

Another sample holder intended for a sample under pressure is illustrated in US published application 2011/0050223. It has a non-magnetic metal tube around the sample to retain pressure. The radio-frequency coil required for NMR is located inside this tube, with the sample placed inside the coil. The metal tube and the end pieces screwed into it provide sufficient strength to resist both radially outward stress (hoop stress) and also longitudinal stress resulting from the internal pressure.

SUMMARY

This summary is provided to introduce a selection of concepts that are further described below. This summary is not intended to be used as an aid in limiting the scope of the subject matter claimed.

One aspect of the subject matter disclosed in this application is a pressurizable holder for a sample to be examined by NMR, comprising a pressure retaining tube formed of material which is non-magnetic and does not provide isotropic electrical conductivity, with this pressure retaining tube surrounding one or more radio-frequency coils which in turn surround a space for the sample.

A tube which does not provide isotropic electrical conductivity may be electrically insulating or may provide conductivity which is anisotropic. Both possibilities will inhibit the induction of eddy currents when there is a change in the magnetic field to which the sample holder is subjected, as happens when gradient coils which impose a magnetic field gradient are switched on and off.

The pressure retaining tube may be formed of non-metallic material and may be electrically non-conductive. Employing a non-metallic electrically insulating material for the pressure retaining tube can prevent induction of unwanted eddy currents in the material of the tube when gradient coils in the NMR spectrometer are switched on and off to superimpose a temporary magnetic field gradient on the main magnetic field of the spectrometer. Locating the radio-frequency coil(s) inside the pressure retaining tube is beneficial, because the sample can occupy a large portion of the cross-sectional area within the coil. This is referred to as a "high coil filling factor" and gives a better signal-to-noise ratio than arrangements with the radio-frequency coil(s) outside a pressure retaining tube. Non-metals are usually avoided when strength is required, but with the coil(s) on the inside, the pressure-retaining tube can be constructed with substantial wall thickness, and thus be able to contain internal pressure, yet without reducing the coil filling factor.

A range of nonmetallic materials may be used for the pressure retaining tube. One possibility is a ceramic material which may be homogenous. Another possibility is an electrically insulating composite comprising an electrically insulating matrix material reinforced with electrically insulating filaments. The matrix may be ceramic or may be an organic polymer and possibilities for insulating filaments include glass fiber.

Another possibility within the present disclosure is that the tube comprises a composite material comprising an electrically insulating matrix material reinforced with conductive filaments such as carbon fibers. Carbon fibers provide good mechanical strength but are electrically conductive along their length, which makes them unacceptable inside a radio-frequency coil. However, this is not an issue when, as disclosed here, the pressure retaining tube surrounds the radio-frequency coil. Going further, if carbon fibers are oriented in a common direction so that they extend generally side by side, even though some may cross at a small angle, the there will be greater conductivity along the fibers than transversely across them, because conduction transverse to the fibers requires a pathway which crosses from one fiber to another. The conductivity of the carbon fibers is anisotropic with the consequence that the carbon fiber reinforced composite inhibits eddy currents when gradient coils are switched on and off. Some limited conductivity transverse to the fiber direction may be acceptable because even this will reduce eddy currents compared to a material which is electrically isotropic and conductive in all directions.

A carbon fiber reinforced composite may comprise an organic polymer as matrix material strengthened by the carbon fibers. Carbon fibers may be the sole reinforcing fibers or may be employed jointly with other fibers such as glass fibers or fibers of poly-paraphenylene terephthalamide—marked under the trade name Kevlar.

It is possible that all carbon fibers are in a common orientation, such as circumferential relative to the tube axis. However, it is also possible that carbon fibers could be arranged in some other way and still be able to resist flow of eddy currents. A possibility is to provide carbon fibers in a plurality of layers within the wall of the pressure retaining tube with different fiber orientations in the layers and spacing between the layers so that carbon fibers in one layer do not make good electrical contact with differently oriented carbon fibers in another layer.

It is also conceivable that metallic fibers could be incorporated into a composite material, provided these were oriented and spaced so that electrical conductivity was anisotropic, that is to say conductive along the fibers but not in the transverse direction through contact between fibers.

The sample contained in a sample holder as above may possibly be a liquid, or may be a solid, such as a rock core which may be a porous rock with liquid in its pores.

In a further aspect of the present disclosure, a pressurizable holder for a liquid sample to be examined by NMR comprises a pressure retaining tube, which may metallic or or may be non-metallic, surrounding one or more radio-frequency coils which in turn surround a non-metallic tube to contain the liquid sample. A space between the pressure retaining tube and the sample-containing tube may be pressurizable so that the tube for the sample does not need to be dimensioned to resist stress. The tube for the liquid sample may contain a movable piston to allow liquid under pressure to make a controlled entry against resistance applied by the piston. Such an arrangement can provide a good coil filling factor within the radio-frequency coil while also providing physical containment of the liquid sample. The tube which contains the liquid sample may be part of a non-metallic vessel or it may have its ends closed by separate parts which may be metallic. Here also a composite material may be used as a material for the pressure retaining tube and the composite may contain carbon fibers as discussed above.

Another aspect of the disclosed subject matter of this application is an NMR spectrometer providing magnetic field with a removable sample holder as above placed in the magnetic field such that the axis of the pressure retaining tube is transverse to the magnetic field and with the radio-frequency coil(s) of the sample holder connected to the spectrometer, so that application of a radio-frequency signal to a coil by the spectrometer induces magnetic resonance of nuclei in a sample within the sample holder.

In a further aspect, the disclosed subject matter provides a method of examining a sample by NMR comprising placing a sample in a sample holder as above, placing the sample holder in an NMR spectrometer such that the axis of the pressure retaining tube is transverse to the magnetic field, connecting the radio-frequency coil(s) of the sample holder to the spectrometer, applying a radio-frequency signal to a coil within the sample holder to induce magnetic resonance of nuclei in the sample, and using the same or another coil within the sample holder to receive radio-frequency emissions from the sample.

A sample holder as discussed above may be provided with structural parts to contain pressure longitudinally relative to the tube, these structural parts comprising pieces to apply force longitudinally at the ends of tube and connecting structure extending between these pieces outside the tube.

The disclosed subject matter also includes an NMR spectrometer providing a magnetic field between a pair of pole pieces spaced from each other and a removable sample holder to be placed in the magnetic field, wherein the sample holder comprises a pressure retaining tube to contain the sample, a pair of end pieces to apply force at the ends of the tube and so retain pressure longitudinally within the tube and least two tie members connecting the end pieces to each other and extending alongside the tube, configured such that the NMR spectrometer accommodates the removable sample holder in the magnetic field between the pole pieces with the tie members extending at either side of the tube at positions spaced laterally, relative to the magnetic field, from the tube axis.

DETAILED DESCRIPTION

Figure 1:
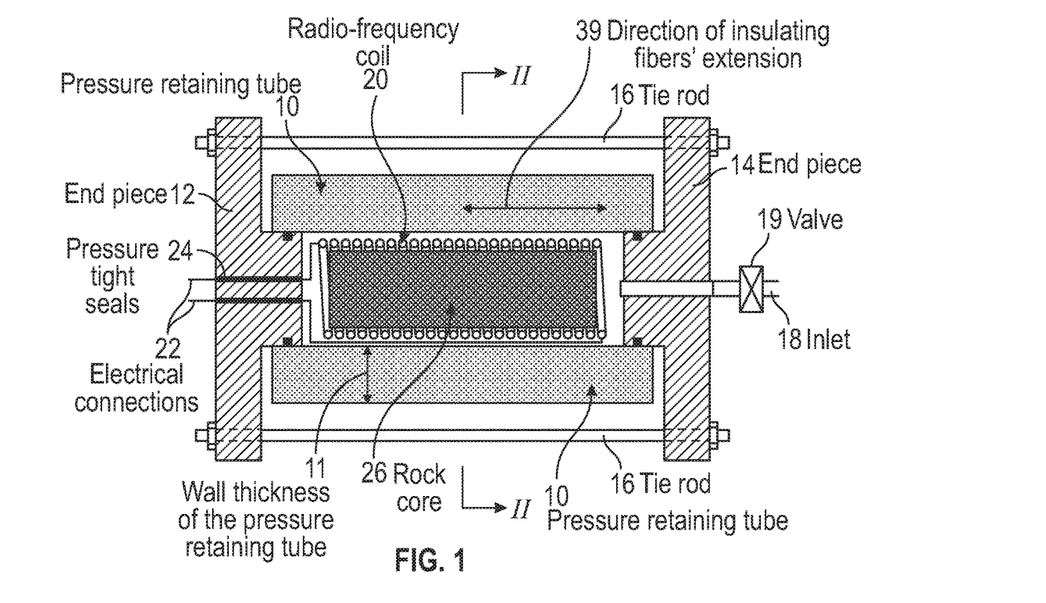
FIG. 1 is a schematic cross-section showing basic parts of a sample holder on line I-I of FIG. 2.
Figure 2:
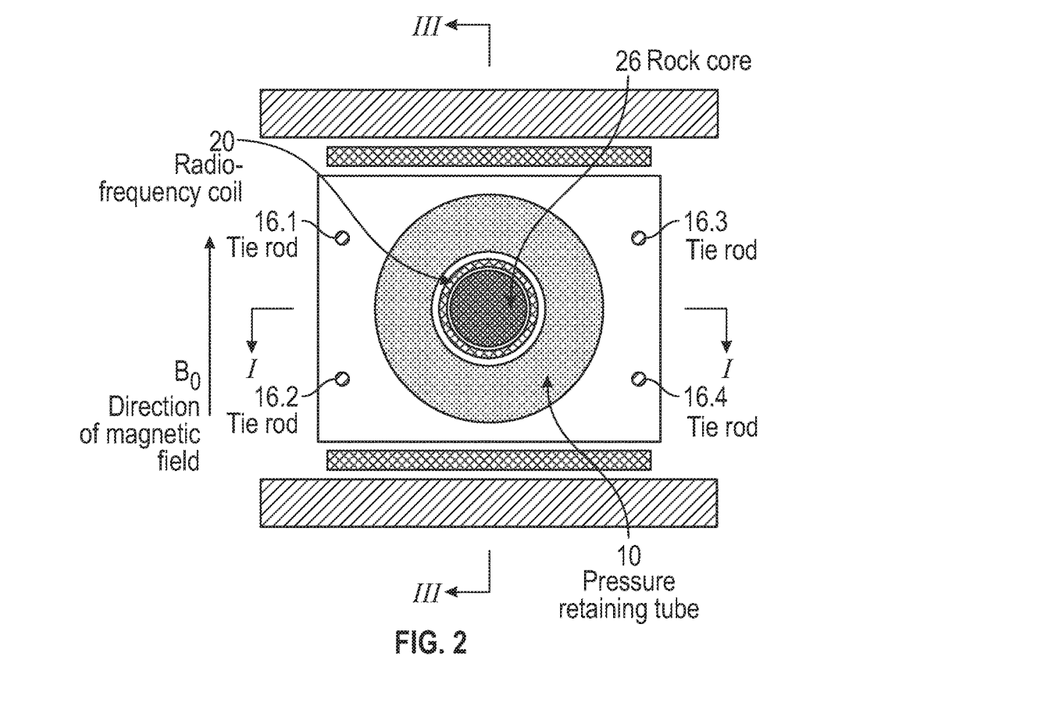
FIG. 2 is a cross sectional view on line II-II of FIG. 1, with the sample holder in the magnetic field of an NMR spectrometer.
Figure 3:
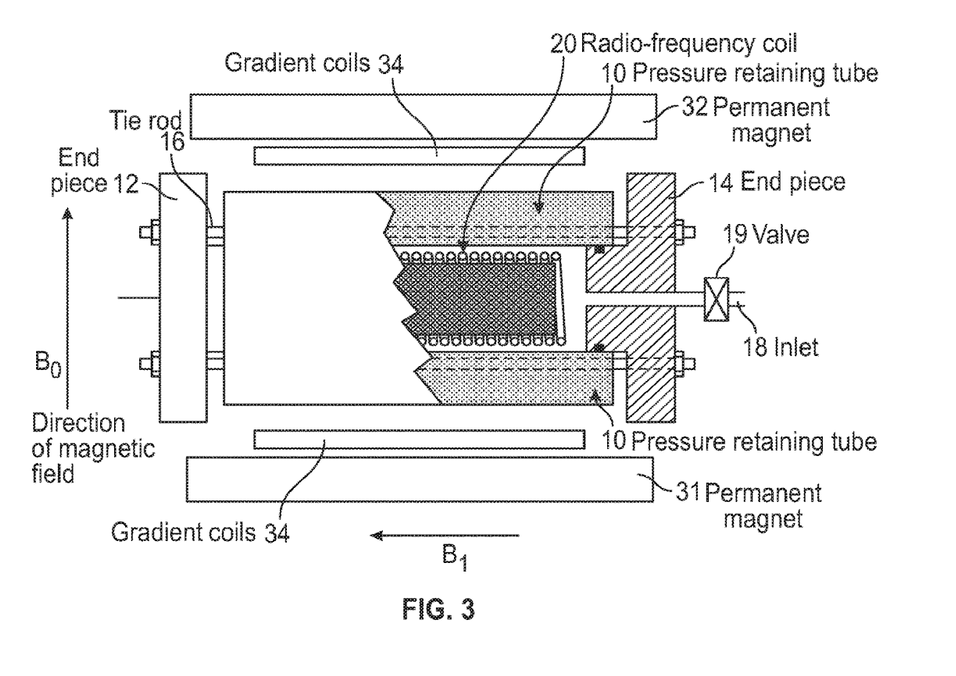
FIG. 3 is partly in section on line III-III of FIG. 2, with the sample holder in the magnetic field of an NMR spectrometer.

The sample holder shown in FIGS. 1 to 3 has a non-metallic pressure retaining tube 10 with substantial wall thickness, indicated by double headed arrow 11, so as to withstand hoop stress, i.e., radially outward pressure from within. Longitudinal stress from internal pressure is restrained by end pieces 12, 14 which are connected together by a four tie rods 16 which are in tension. Thus the tube 10 is not required to provide longitudinal strength. Both end pieces 12, 14 may be removable and sealed to the tube by O-rings as shown or the tube 10 could be permanently attached to one of the end pieces.

Fluid to pressurize the interior space within the tube 10 is admitted through an inlet 18 which can be closed by a valve 19. A radio-frequency coil 20, which is generally cylindrical is located within the tube 10 and is close to its inside wall. The coil 20 is shown schematically as a single helical solenoid coil but it may be wound with multiple layers. It is possible that there could be more one coil, for example one coil as an emitter and one as an antenna with the two coils wound one on top of the other. It is also possible that other configurations of coil(s) could be employed such as a pair of saddle coils with a space for the sample between them. A cylindrical rock core 26 which is to be examined by NMR fits within the interior of the coil 20.

Electrical connections 22 to the coil 20 are led out through pressure tight seals 24 in the end piece 12. Devices for electrical feed through a pressure barrier are known. One possibility is single pin feed thru connectors available from Kemlon Products Inc., Pearland, Tex.

FIGS. 2 and 3 show the sample holder in position within an NMR spectrometer. This spectrometer has a pair of disc shaped permanent magnets 31, 32 facing each other but spaced apart so that a magnetic field extends in the direction indicated by the arrow $B_0$ in FIG. 2. Both permanent magnets 31, 32 may be made of rare earth compounds to give a high magnetic field. Specifically, they may possibly be neodymium iron boron (NdFeB) magnets which can be manufactured in the desired shapes or assembled from smaller blocks.

Gradient coils 34 are positioned adjacent the magnets 31, 32. When these gradient coils 34 are energised, a magnetic field with a gradient along the length of these coils, i.e., as indicated by arrow $B_1$ is superimposed on the static field $B_0$. This field gradient is proportional to the current in the coils 34 and its magnitude can thus be controlled.

The pressure retaining tube 10 of the sample holder is positioned in the magnetic field between the gradient coils 34 and parallel to them. As best seen from FIG. 2, the tie rods at either side of the tube are then located at positions which are spaced laterally from the axis of tube 10.

FIG. 2 shows that the geometry can be compact. The four tie rods 16, which are indicated as 16.1 to 16.4 in FIG. 2, are at a radial distance from the axis of tube 10 which is approximately the same as the distance from the tube axis to the magnets 31, 32. The tie rods 16.1 and 16.2 are spaced from the axis of the tube 10 and from the tie rods 16.3 and 16.4 in directions transverse to the magnetic field $B_0$. The spacing between the tie rods 16.1 and 16.3 is equal to spacing between rods 16.2 and 16.4, and is approximately 1.25 times the external diameter of the tube 10. It is thus less than double, moreover less than 1.5 times, the external diameter of the tube 10. The spacing in the direction of the magnetic field $B_0$ between the tie rods 16.1 and 16.2 is equal to spacing between rods 16.3 and 16.4 and is less than the spacing between the magnets 31, 32. Moreover, it is less than the diameter of the tube 10.

As can be appreciated from FIGS. 1-3, the various parts are dimensioned such that a core 26 of standard diameter fills most of the available cross-section within the coil 20. Thus the coil filling factor is high. It is possible for the pressure retaining tube 10 to have substantial wall thickness because coil filling factor is independent of this thickness. Consequently a number of non-metallic materials can be used for the tube 10. One possibility is an inorganic ceramic material. Another possibility is a fiber-reinforced composite in which elongate fibers are bound in a matrix material which may be an inorganic ceramic or may be an organic polymer. Glass reinforced polymer (GRP) and carbon fiber reinforced polymer (CFRP) are examples of composite materials. An organic polymer matrix of a composite material may be any of a number of polymers including epoxy resin and polyetherether ketone (PEEK) which is well established as an engineering plastic.

Figure 4:
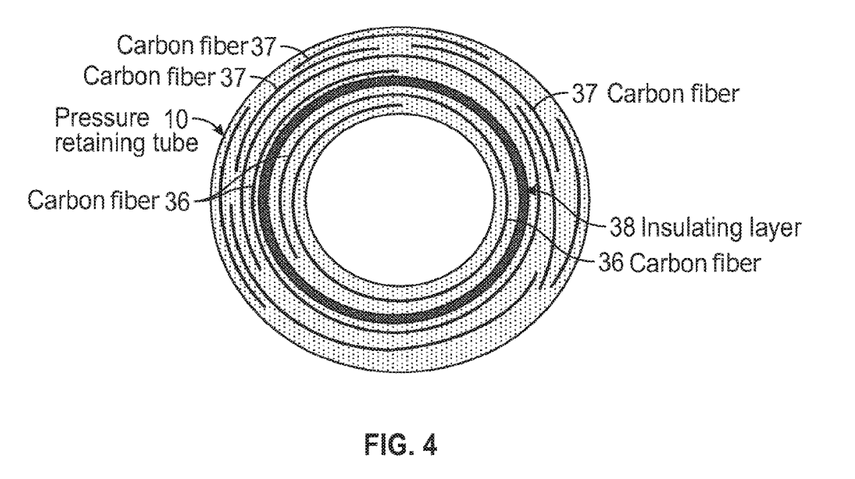
FIG. 4 is a cross section through the pressure-retaining tube, showing an example of the orientation of reinforcing fibers.

FIG. 4 is a cross section through a pressure retaining tube 10 which is a composite reinforced with carbon fiber. Carbon fibers are conductive, but can be used in the wall of tube 10 because it is outside the coil 20. The carbon fibers 36, 37 are shown with exaggerated thickness for the purpose of explanation. The carbon fibers within the wall of the tube 10 extend circumferentially around the central axis of the tube 10 but extend only slightly, if at all, in the axial direction of the tube. In this orientation the fibers are best placed to withstand hoop stress. Fibers may extend around the axis for a full circle of 360 degrees or more, as illustrated by the fibers 36 or they may extend as arcs of less than 360 degrees, as illustrated by the fibers 37. A layer 38 of glass fibers is included within the thick wall of the tube 10. These insulating fibers extend axially (the direction indicated by double headed arrow 39 in FIG. 1) to increase strength of the tube 10 in its longitudinal direction. This axial strengthening is not required for resisting internal pressure, but makes the tube 10 more robust during handling and assembly of the sample holder.

Because the conductive carbon fibers are oriented in a common, circumferential direction, the electrical conductivity within the wall of the tube 10 is anisotropic, with much less conductivity in the axial direction than circumferentially around the tube axis. Consequently, turning the gradient coils 34 on and off will not generate eddy currents to the same extent as in a material which is fully conductive in all directions because the electrical resistivity transverse to the fibers' orientation, i.e., in the axial direction, will inhibit current flow and thus inhibit circulation of eddy currents.

It has been reported in the literature that conductivity in the direction of carbon fibers may be greater than conductivity transverse to the fibers by a factor which is dependent on composition and manufacturing procedures, but this factor may be 100 or considerably more. Conductivity transverse to fibers is dependent on the volume fraction of carbon fibers in the composite. If carbon fibers lying in a common orientation are no more than about 30 to 40% by volume of the composite, conductivity transverse to the fibers may be very small. See for instance Pratap et al., IEEE Transactions on Magnetics, Vol. 32, March 1996, pp. 437-444 at page 438. Park et al., Smart materials and Structures, Vol. 16, 2007, pp. 57-66 at page 61 measured conductivities along and transverse to fibers at a number of volume fractions, and even at a volume fraction of 55 to 60% carbon fiber oriented in a common direction the conductivity along the fibers was several orders of magnitude greater than conductivity transverse to them.

There are a number of ways to arrange reinforcing fibers in the wall of tube 10 to incorporate carbon fiber and achieve anisotropic conductivity. Carbon fibers may be used throughout the wall of tube 10 or in layers within the wall of tube 10 where the only reinforcing fibers are carbon fibers in a common orientation. Alternatively carbon fibers might be mixed with non-conducting fibers such as glass or Kevlar, for example using sufficient non conducting fibers that the volume fraction of carbon fibers is below 50% of the composite but the total of all fibers was a volume fraction above 50%, such as 55 to 60% of the composite If glass fibers are included, they may be confined to a layer such as layer 38 or may be distributed more generally. They may extend axially as described or predominantly axially but also a layer of glass fibers could be a mat of randomly oriented fibers. Carbon fibers could be arranged in layers such that the fibers in each layer are in a common orientation, but with different orientations in different layers so that anisotropic conductivity in one layer is in a different direction from that in another, provided conductivity between layers is low. Thus with circumferentially oriented carbon fibers as shown in FIG. 4 it would be possible to incorporate carbon fibers extending axially, provided they were electrically insulated from the circumferential fibers, such as in a separate layer akin to the layer 38.

Another possibility for the arrangement of carbon fibers would for example be a layer of carbon fibers extending as a right handed helix, overlaid with an insulating layer 38, which in turn is overlaid with carbon fibers in a left handed helix.

Figure 5:
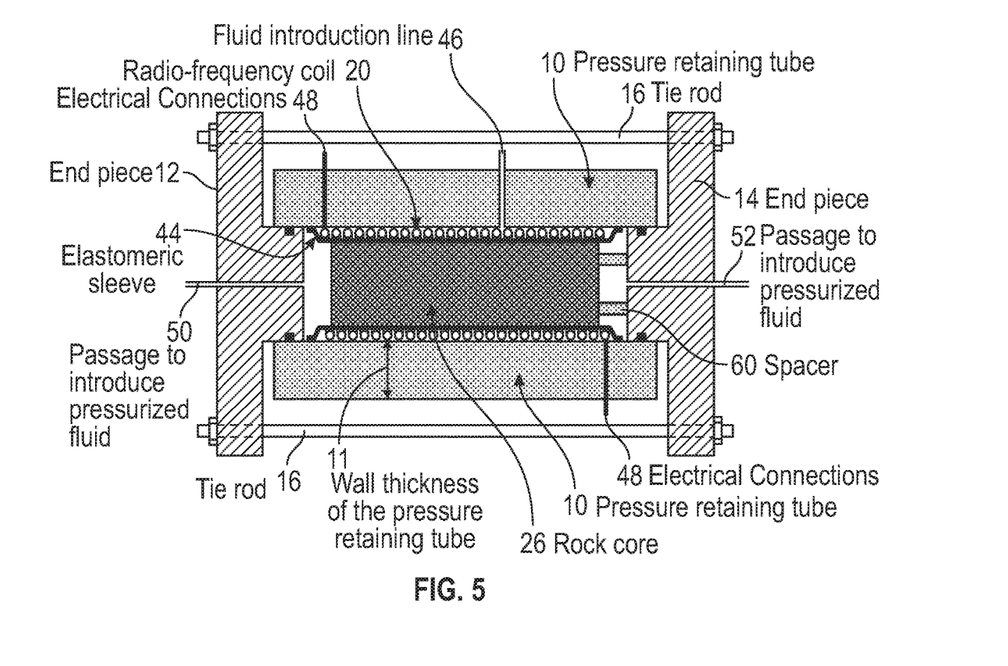
FIG. 5 is a cross section of an example sample holder with provision for liquid flow.

FIG. 5 shows an arrangement in which a number of features are the same as in FIGS. 1 to 3, and are indicated with the same reference numerals. In this embodiment, the cylindrical surface of the core 26 is enclosed by an elastomeric sleeve 44. This sleeve 44 is urged against the cylindrical surface of the core 26 by a fluid introduced along line 46 to fill the space between the sleeve 44 and the inside wall of tube 10. This fluid may be a perfluorocarbon so that the fluid does not contain hydrogen atoms and does not give any signal when NMR is used to examine resonance of hydrogen nuclei. Consequently, the end faces of the core 26 are exposed but the cylindrical surface of the core is sealed by the elastomeric sleeve 54. Electrical connections 48 to the coil 20 extend radially through the wall of tube 10, either extending through feed through connectors or sealingly embedded in the material of the tube wall.

Fluid to pressurize the interior of the tube 10 can be introduced along passages 50 and 52 which extend through the end members 12 and 14. It is also possible to flow fluid linearly through the core 26, using passage 50 as an inlet for fluid under pressure while maintaining a slightly lower pressure in passage 52. At least one spacer piece 64, made of non-magnetic and electrically insulating material is used to keep the core 26 in position. Such a spacer piece may be made of a porous material or may incorporate apertures, to allow flow out of the end face of the core 26 to reach the passage 52.

Figure 6:
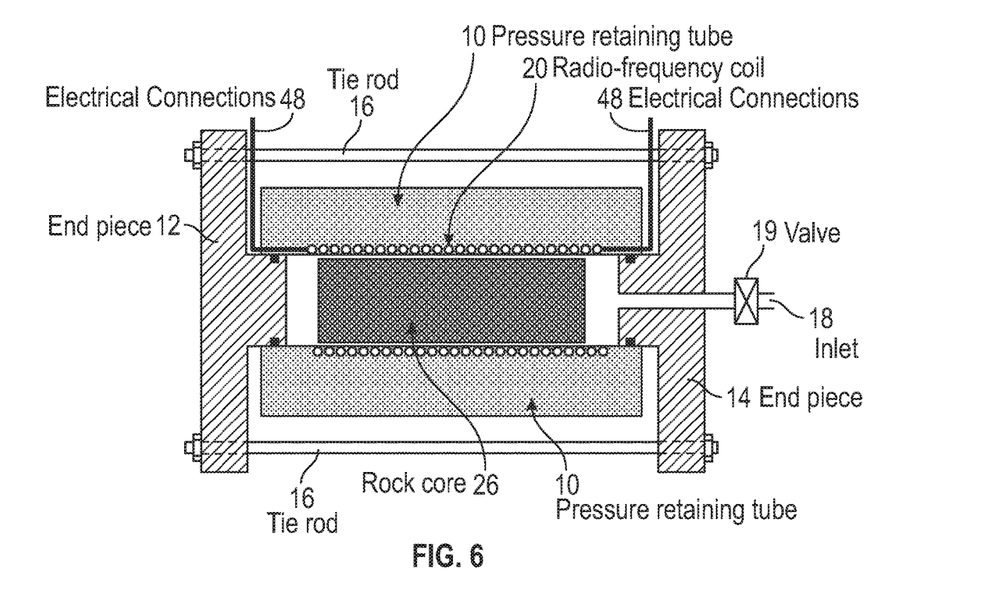
FIG. 6 is a schematic cross-section of another example sample holder.

FIG. 6 shows a variation of the arrangement of FIGS. 1 to 3. The coil 20 is embedded within the material of the tube 10 close to its internal face. Electrical connections 58 to the coil 20 are led out at the ends of tube 10. With such an arrangement the material of the tube 10 which is positioned inwardly from the coil 20 could contribute to the NMR signal obtained. For example, if the intention is to observe resonance of hydrogen atoms in the core 26, hydrogen atoms (if any) in the thin layer of tube 10 which is positioned inwardly from the coil 20 make a small and constant contribution to the NMR signals. One possibility for avoiding this is to make the tube 10 from an inorganic ceramic material or a composite which is a fiber reinforced inorganic ceramic. Such a material may have no hydrogen atoms in its composition and therefore provide no NMR signal when the resonance of hydrogen nuclei is being examined.

Figure 7:
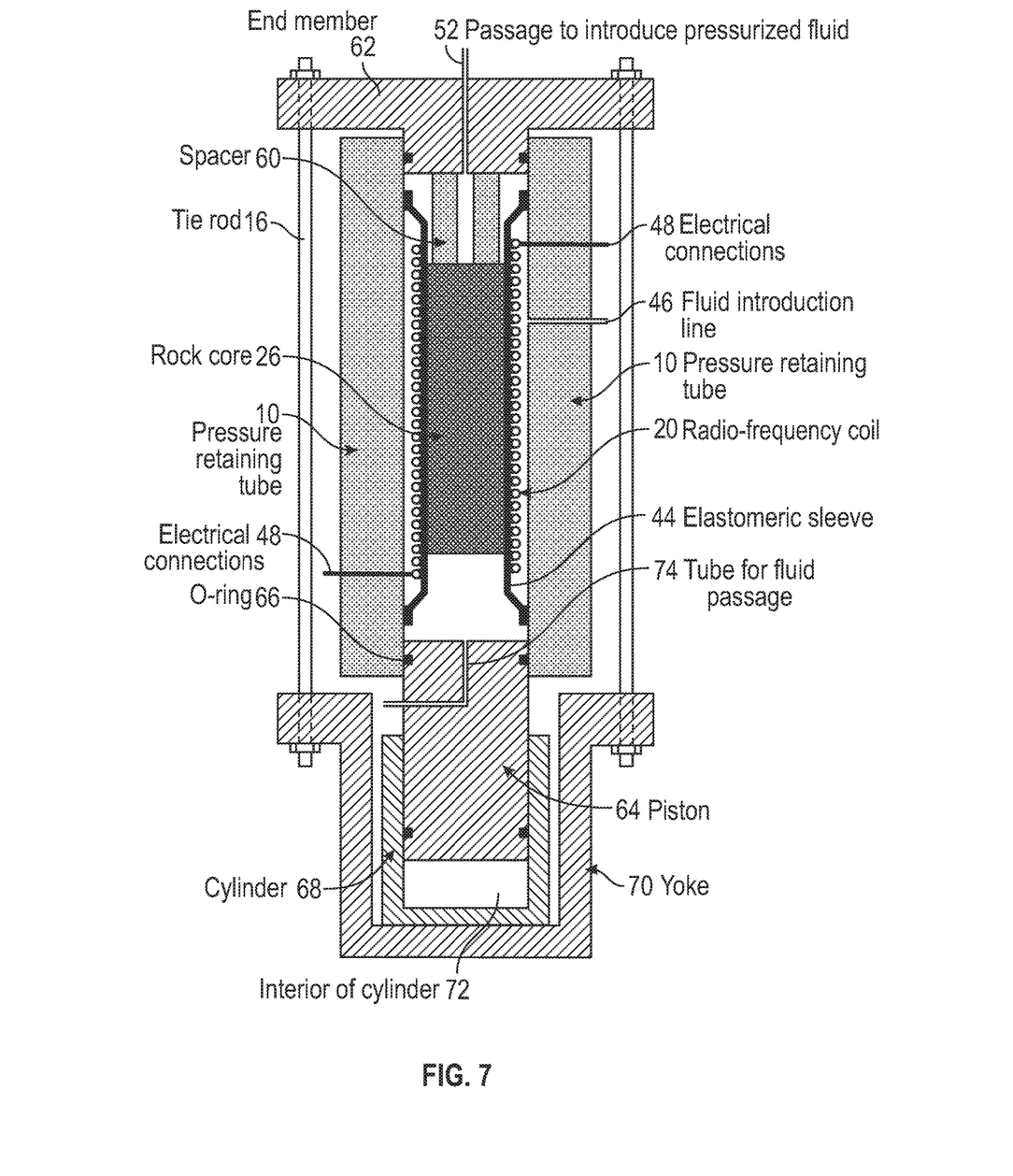
FIG. 7 is a schematic cross-section of a further example sample holder.

FIG. 7 shows a further possible arrangement. The pressure retaining tube 10 is again made of non-magnetic material, dimensioned to withstand hoop stress. It is closed at one end by an end member 62 which is generally similar to the end members 12, 14 shown in FIG. 1. The other end of the tube 10 is closed by a piston 64 which is a sliding fit within tube 10 and sealed to it by O-ring 66. The piston 64 also slides within a cylinder 68 supported by yoke 70 which in turn is connected to the end member 62 by tie rods 16. Thus, longitudinal stress from pressure within the tube 10 is retained by the tie rods 16 which are in tension, connecting the end member 62 to the yoke 70. The space within the tube 10 can be pressurized by supplying hydraulic oil through an inlet, not shown, to the interior 72 of cylinder 68 so as to urge the piston 64 into the tube 10.

A radio-frequency coil 20 is positioned within the tube 10. A rock core 26 can be received within the space within the coil 20. In this embodiment, the cylindrical surface of the core 26 is enclosed by an elastomeric sleeve 44 which, as in FIG. 5, is urged against the cylindrical surface of the core 26 by a fluid introduced along line 46. This fluid may be a perfluorocarbon so that the fluid does not contain hydrogen atoms. Consequently, the end faces of the core 26 are exposed to fluid in the tube 10 but the cylindrical surface of the core is sealed by the elastomeric sleeve 44. Tubes 74 and 52 allow the interior of tube 10 to be filled with fluid. If desired, fluid can be made to flow linearly through the core 26. For this fluid is supplied along tube 74 to enter one end face of the core and fluid leaving through the other end face of the core leaves through tube 52. As in FIG. 5, a spacer 60 is provided between the core 26 and the end piece 62.

As in FIGS. 1 to 3 the core 26 fills most of the cross-section within the coil 20. The core holder with the core 26 located within the coil 20 can be placed between the magnets of an NMR spectrometer in the same manner as is shown by FIGS. 2 and 3.

Figure 8:
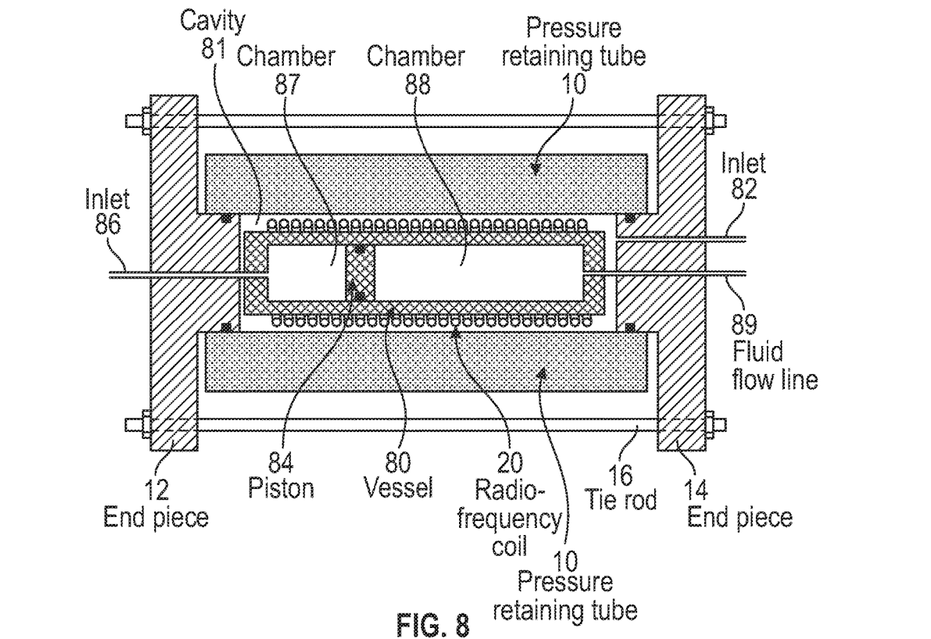
FIG. 8 is a schematic cross-section of an example sample holder able to receive liquid under pressure.

FIG. 8 shows a sample holder for a liquid sample which is required to be kept under pressure. The general arrangement has similarity to that in FIGS. 1 to 3. A pressure retaining tube 10 contains hoop stress, while longitudinal stress is contained by end members 12, 14 connected by tie rods 16 which are in tension. There is a radio-frequency coil 20 within the tube 10.

Inside the radio-frequency coil there is a cylindrical vessel 80 made of an inorganic ceramic material. This is non-magnetic and electrically insulating. A suitable material is magnesia stabilized zirconia. Dynamic-Ceramic Ltd of Crewe, UK supply this under the name Technox 500 as a raw material for fabricating ceramic articles. This vessel 80 is constructed as a rigid vessel able to sustain its own shape and provide a container for liquid, but with thin walls so that it does not take up an excessive amount of the cross section within the coil 20. The generally annular cavity 81 between the vessel 80 and the tube 10, which contains the coil 20, is pressurized with a fluid admitted through inlet 82. This fluid may be a perfluorocarbon so that it does not contain hydrogen atoms. The cavity 81 is pressurized to a pressure which is that same as, or close to, pressure inside the vessel 80. By balancing pressure inside and outside the vessel 80, it does not need to be constructed as a pressure vessel with thick walls.

In order to admit a sample fluid under pressure, the vessel 80 encloses an internal floating piston 84. The sample fluid is admitted under pressure along line 86 to the chamber 87 at one side of the piston 84 while the chamber 88 at the other side of floating piston 84 is pressurized with fluid supplied along line 89. This fluid may be the same as that supplied through inlet 82 to space 81. The pressure in chamber 88 is reduced to slightly less than the pressure of the incoming sample entering through inlet 86, so that the incoming sample slowly drives the piston 84 along the vessel 80, expelling fluid along line 89 until vessel 80 is filled with the sample fluid. The cavity 81 may be connected to the vessel 80 at one side or other of the piston 84 so that pressure in the vessel is communicated to the cavity 81 and thus pressure in the cavity is automatically balanced with a pressure in the vessel 80. A connection to the cavity 81 may allow communication of pressure to cavity 81 without permitting fluid to flow from the vessel 80 into the cavity 81. Thus sample liquid may be excluded from cavity 81.

Figure 9:
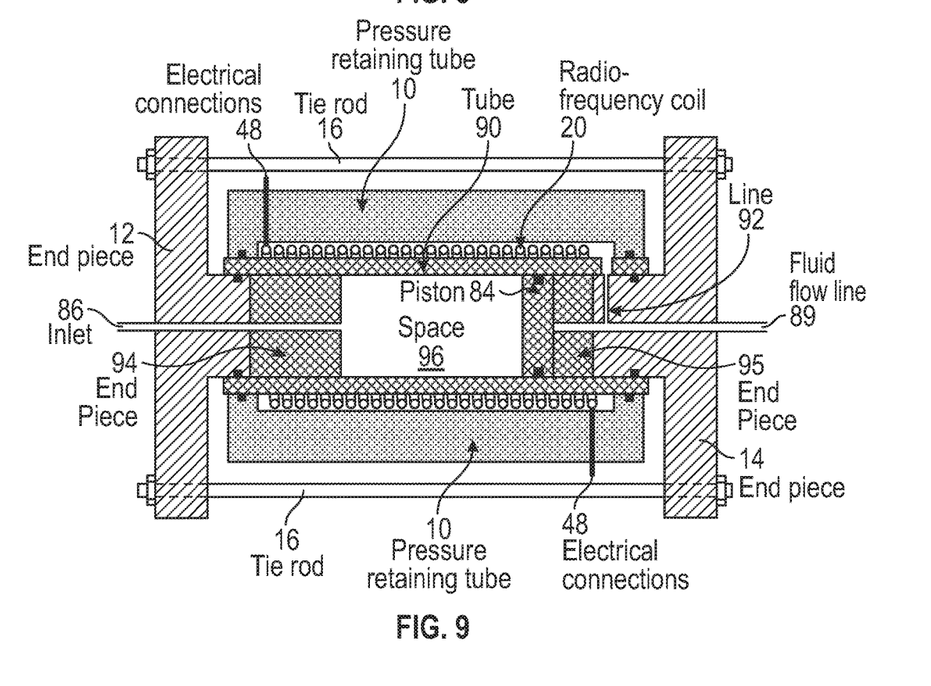
FIG. 9 is a schematic cross-section of a second example of sample holder able to receive liquid under pressure.

FIG. 9 illustrates an arrangement which is similar in principle (and equivalent parts are indicated with the same reference numerals) but has a tube 90 (which is made of magnesia stabilized zirconia) closed by the end members 12, 14 to receive the liquid sample. This tube 90 is again a rigid tube able to sustain its own shape and enclose liquid. It is surrounded by a pressure retaining tube 10 with the coil 20 in a cavity which is pressurized with perfluorocarbon fluid via line 92 which connects to line 89. Thus the cavity outside tube 90 is at the pressure of (and is filled by) the perfluorocarbon fluid which is expelled from tube 90 as the sample fluid enters and drives the floating piston 84 along the tube 90.

Within the tube 90 there are end pieces 94, 95 which occupy space at each end of the interior of tube 90. When the sample has been introduced through inlet 86 and the floating piston 84 has been driven fully along the tube 90 so that it abuts end piece 95 as shown, the volume occupied by the sample is the space 96 within a middle part of the length of coil 20. Consequently the liquid sample is spaced from any distortions of the radio-frequency field near the ends of the coil 20.

The purpose of using NMR to examine a liquid sample may be to observe diffusion within the liquid, for which a magnetic field gradient provided by gradient coils 34 will be employed. Consequently, in FIGS. 8 and 9 the pressure retaining tube 10 may be made of non-metallic and electrically insulating material such as the ceramic and composite materials already mentioned. In the event that the NMR examination of a liquid sample does not require a magnetic field gradient, so that gradient coils 34 will not be present, or will not be operated if present, the pressure retaining tube 10 of these embodiments could be made of a non-magnetic metal such as stainless steel.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:

1. A nuclear magnetic resonance (NMR) pressurizable sample holder configured for retaining a fluid sample during a performance of an NMR examination, comprising
   a pressure-retaining nonmagnetic tube formed of non-metallic electrically insulating matrix material which is reinforced with electrically conductive filaments that are configured and arranged within the non-metallic electrically insulating matrix material to directionally inhibit induced eddy currents by having less conductivity in a direction transverse to the reinforcing electrically conductive filaments than in a direction along a length of the reinforcing electrically conductive filaments;
   gradient coils that are spaced around the pressure retaining nonmagnetic tube, wherein the gradient coils are configured to be switched on and off during the performance of the NMR examination, and where the gradient coils generate the induced eddy currents that the reinforcing electrically conductive filaments are configured and arranged to directionally inhibit;
   the pressure-retaining nonmagnetic tube also being positioned to surround at least one radio-frequency coil, and the at least one radio-frequency coil being positioned to surround a space configured for retaining the fluid sample.

2. The nuclear magnetic resonance (NMR) pressurizable sample holder of claim 1, wherein the pressure-retaining nonmagnetic tube formed of non-metallic electrically insulating matrix material and reinforced with electrically conductive filaments is also reinforced with non-metallic electrically insulating reinforcing filaments.

3. The nuclear magnetic resonance (NMR) pressurizable sample holder of claim 1, wherein the pressure-retaining nonmagnetic tube formed of non-metallic electrically insulating matrix material is formed of a non-metallic composite material comprising electrically insulating matrix material that is reinforced with carbon fibers as the electrically conductive filaments.

4. The nuclear magnetic resonance (NMR) pressurizable sample holder of claim 1, wherein the pressure retaining nonmagnetic tube formed of non-metallic electrically insulating matrix material is formed of a non-metallic composite material comprising electrically insulating matrix material that is reinforced with carbon fibers as the electrically conductive filaments, and additionally reinforced with electrically insulating fibers.

5. The nuclear magnetic resonance (NMR) pressurizable sample holder of claim 1, wherein the non-metallic electrically insulating matrix material is an organic polymer.

6. The nuclear magnetic resonance (NMR) pressurizable sample holder of claim 1, further comprising:
   a plurality of end pieces that are arranged in order to apply force longitudinally at the ends of the pressure-retaining nonmagnetic tube; and
   a connecting structure extending between the end pieces, where the connecting structure is located and positioned outside of the pressure-retaining nonmagnetic tube.

7. The nuclear magnetic resonance (NMR) pressurizable sample holder of claim 6, wherein the connecting structure is located and positioned outside of the pressure-retaining nonmagnetic tube such that a maximum radial distance of the connecting structure from an external diameter of the pressure-retaining nonmagnetic tube is not more than twice the external diameter of the pressure-retaining nonmagnetic tube.

8. The nuclear magnetic resonance (NMR) pressurizable sample holder of claim 1, wherein the at least one radio-frequency coil surrounds an electrically insulating tube having the form of an elastomeric sleeve in order to contain a liquid sample.

9. The nuclear magnetic resonance (NMR) pressurizable sample holder of claim 8, wherein a pressurizable space between the pressure-retaining nonmagnetic tube and the electrically insulating tube having the form of the elastomeric sleeve in order to contain the liquid sample also contains the at least one radio-frequency coil.

10. The nuclear magnetic resonance (NMR) pressurizable sample holder of claim 8, wherein the electrically insulating tube having the form of the elastomeric sleeve in order to contain the liquid sample also contains a movable piston in order to separate the liquid sample from a pressure controlling liquid that is maintained under pressure as the liquid sample enters the electrically insulating tube having the form of the elastomeric sleeve at a higher pressure.

11. The nuclear magnetic resonance (NMR) pressurizable sample holder of claim 10, wherein a pressurizable space between the pressure-retaining nonmagnetic tube and the electrically insulating tube having the form of the elastomeric sleeve in order to contain the liquid sample also contains the at least one radio-frequency coil and is configured to be in pressure communication with the pressure controlling liquid.

12. A nuclear magnetic resonance (NMR) spectrometer providing a magnetic field and having an NMR pressurizable sample holder as claimed in claim 1, which is placed in the provided magnetic field such that the axis of the pressure-retaining nonmagnetic tube is transverse to the provided magnetic field, and having the at least one radio-frequency coil of the NMR pressurizable sample holder connected to the NMR spectrometer, so that application of a radio-frequency signal to the at least one RF coil by the NMR spectrometer induces magnetic resonance of nuclei in a fluid sample located or positioned within the NMR pressurizable sample holder.

13. A method of examining a sample by nuclear magnetic resonance (NMR) comprising:
    placing a fluid sample in an NMR pressurizable sample holder as claimed in claim 1;
    placing the NMR pressurizable sample holder in an NMR spectrometer, providing a magnetic field such that the axis of the pressure-retaining tube is transverse to the provided magnetic field;
    connecting the at least one radio-frequency coil of the NMR pressurizable sample holder to the NMR spectrometer;
    applying a radio-frequency signal to the at least one radio-frequency coil in order to induce magnetic resonance of nuclei in the fluid sample located or positioned within the NMR pressurizable sample holder; and
    using the at least one radio-frequency coil in order to receive radio-frequency emissions from the fluid sample.

14. A nuclear magnetic resonance (NMR) spectrometer providing a magnetic field and having an NMR pressurizable sample holder as claimed in claim 8, which is placed in the provided magnetic field such that the axis of the pressure-retaining nonmagnetic tube is transverse to the provided magnetic field and having the at least one radio-frequency coil of the NMR pressurizable sample holder connected to the NMR spectrometer, so that application of a radio-frequency signal to the at least one RF coil by the NMR spectrometer induces magnetic resonance of nuclei in a liquid sample located or positioned within the NMR pressurizable sample holder.

15. A method of examining a sample by nuclear magnetic resonance (NMR) comprising:
    placing a liquid sample in a nuclear magnetic resonance (NMR) pressurizable sample holder as claimed in claim 8;
    placing the nuclear magnetic resonance (NMR) pressurizable sample holder in an NMR spectrometer such that the axis of the pressure-retaining nonmagnetic tube is transverse to the magnetic field;
    connecting the at least one radio-frequency coil of the NMR pressurizable sample holder to the NMR spectrometer;
    applying a radio-frequency signal to the at least one radio-frequency coil in order to induce magnetic resonance of nuclei in the liquid sample located or positioned within the NMR pressurizable sample holder; and
    using the at least one radio-frequency coil in order to receive radio-frequency emissions from the liquid sample.

* * * * *